United States Patent [19]

Robinson et al.

[11] 4,369,530

[45] Jan. 25, 1983

[54] HYDRAULICALLY ACTUATED CARDIAC PROSTHESIS AND METHOD OF ACTUATION

[75] Inventors: Thomas C. Robinson; Sotiris Kitrilakis, both of Berkeley, Calif.

[73] Assignee: Foxcroft Associates, San Antonio, Tex.

[21] Appl. No.: 265,100

[22] Filed: May 19, 1981

[51] Int. Cl.³ .......................... A61F 1/24; A61M 1/03
[52] U.S. Cl. ........................................ 3/1.7; 128/1 D;
417/388; 417/394; 417/395
[58] Field of Search ............. 3/1.7; 128/1 D, DIG. 3; 417/383, 388-390, 394, 395

[56] References Cited

U.S. PATENT DOCUMENTS

| | | | |
|---|---|---|---|
| 3,182,335 | 5/1965 | Bolie | 3/1.7 |
| 3,208,448 | 9/1965 | Woodward | 3/1.7 X |
| 3,273,594 | 9/1966 | Mayer | 3/1.7 X |
| 3,327,322 | 6/1967 | Norton | 3/1.7 |
| 3,337,878 | 8/1967 | Bolie | 3/1.7 |
| 3,434,162 | 3/1969 | Wolfe | 3/1.7 |
| 3,449,767 | 6/1969 | Bolie | 3/1.7 |
| 3,452,738 | 7/1969 | Jones | 128/1 D |
| 3,452,739 | 7/1969 | Guarino | 128/1 D |
| 3,456,444 | 7/1959 | Rishton | 128/1 D X |
| 3,457,909 | 7/1969 | Laird | 128/1 D |
| 3,465,746 | 9/1969 | Guarino | 128/1 D |
| 3,478,695 | 11/1969 | Goranson et al. | 3/1.7 X |
| 3,484,616 | 12/1969 | Baumgardner et al. | |
| 3,487,784 | 1/1970 | Rafferty et al. | 128/1 D X |
| 3,518,702 | 7/1970 | La Russa | 3/1.7 |
| 3,536,423 | 10/1970 | Robinson | 3/1.7 X |
| 3,541,612 | 11/1970 | Carney | 3/1.7 |
| 3,550,162 | 12/1970 | Huffman et al. | 3/1.7 |
| 3,568,214 | 3/1971 | Goldschmied | 3/1.7 |
| 3,597,766 | 8/1971 | Buck | 3/1.7 |
| 3,599,244 | 8/1971 | Wortman | 3/1.7 |
| 3,641,591 | 2/1972 | Kolff | 3/1.7 |
| 3,718,044 | 2/1973 | Joyce, Jr. et al. | 3/1.7 X |
| 3,720,199 | 3/1973 | Rishton et al. | 128/1 D |
| 3,755,825 | 9/1973 | DeBakey et al. | 3/1.7 |
| 3,771,173 | 11/1973 | Lamb, Jr. | 3/1.7 |
| 3,771,174 | 11/1973 | Wortman | 3/1.7 |
| 3,783,453 | 1/1974 | Bolie | 3/1.7 |
| 3,791,769 | 2/1974 | Kovacs | 3/1.7 X |
| 3,911,898 | 10/1975 | Leachman, Jr. | 3/1.7 X |
| 3,916,449 | 11/1975 | Davis | 3/1.7 |
| 3,919,722 | 11/1975 | Harmison | 3/1.7 |
| 3,955,557 | 5/1976 | Takagi | 3/1.7 X |
| 3,974,854 | 8/1976 | Kurpanek | 3/1.7 X |
| 4,004,299 | 1/1977 | Runge | 3/1.7 |
| 4,058,857 | 11/1977 | Runge et al. | 3/1.7 |
| 4,143,661 | 3/1979 | LaForge et al. | 3/1.7 X |
| 4,173,796 | 11/1979 | Jarvik | 3/1.7 |
| 4,222,127 | 9/1980 | Donachy et al. | 3/1.7 |

OTHER PUBLICATIONS

"A Totally Implantable Mechanical Heart", by L. M. Smith et al., *Proceedings European Society for Artificial Organs*, vol. 2, pp. 150–153, Nov. 20–22, 1975.

"The Total Artificial Heart", by R. K. Jarvik, *Scientific American*, vol. 244, No. 1, Jan. 1981, pp. 3, 4 and 74–80.

"Development of an Electrical Energy Converter for Circulatory Devices", by J. A. Chambers et al., *NTIS* Publication No. PB-245,042, May 1965, Dept. of Commerce.

Schuder, J. C., Stephenson, H. E., Jr., and Townsend, J. F., "Energy Transport Into a Closed Chest by Means of Stationary Magnets and a Portable High-Power Oscillator", *ASAIO*, vol. VII, 1961, pp. 327–331.

Kwan-Gett, C., Zwart, H. H. J., Kralios, A. C., Kessler, T., Backman, K., and Kolff, W. C., "A Prosthetic Heart with Hemispherical Ventricles Designed for Low Hemolytic Action", pp. 409–415, *Trans. ASAIO*, vol. XVI, 1970.

Akutsu, T., and Kolff, W. J., "Permanent Substitute for Valves and Hearts", *Trans. ASAIO*, vol. 4, pp. 230–235, 1958.

Burns, W. H., Loubier, R., and Bergstedt, R., "Development of an Electrohydraulic Implantable Artificial Heart", *Trans. ASAIO*, vol. XI, pp. 265–268, 1965.

Kolff, W. M., "An Artificial Heart Inside the Body", *Scientific American*, vol. 213, No. 5, Nov. 1965.

Burns, W. H., Loubier, R. J., and Farlow, J. M., "The Development of an Intrapericardial Cardiac Replacement Phase II", *Trans. ASAIO*, vol. XII, pp. 272–274, 1966.

Rogers, A., Williams, K. R., Morris, L. B., "Hydraulic Control of an Artificial Heart", *Surgical Forum*, vol. 17, pp. 159–161, 1966.

Burns, W. H., Schumacher, H. B., Jr., and Loubier, R.

J., "The Totally Implantable Mechanical Heart, An Appraisal of Feasibility", *Annals of Surgery*, pp. 445-456, Sep. 1966.

Griffith, N., and Burns, W. H., "Development of an Electro-Hydraulic Energy Source to Power and Control Circulatory Assist Devices", *Artificial Heart Progress Conference*, pp. 953-968, NIH, Washington, 1969.

Burns, W. H., Schumacher, H. B., Jr., and Griffith, N. J., "The Total Mechanical Cardiac Substitute", *Progress in Cardiovascular Diseases*, vol. XII, pp. 302-322, Nov. 1969.

Schuder, J. C., Gold, J., and Stephenson, H. E., Jr., "Ultra High Power Electromagnetic Energy Transport Into the Body", *Trans. ASAIO*, vol. XVII, pp. 406-410, 1971.

Burns, W., and Griffith, N., "Energy Systems for Implantable Circulatory Assist Devices", Oct. 1971, NTIS No. PB-212-928.

Kwan-Gett, G. S., von Kampen, K. R., Kawai, J., Eastwood, N., Kolff, W. J., "Results of Total Artificial Heart Implantation in Calves", *The Journal of Thoracic and Cardiovascular Surgery*, vol. 62, No. 6, pp. 880-889, Dec. 1971.

Landis, D. L., Pierce, W. S., Rosenberg, G., Donachy, J. H., and Brighton, J. A., "Long-Term In Vivo Automatic Electronic Control of the Artificial Heart", *Trans. ASAIO*, vol. XXIII, pp. 519-525, 1977.

Poirier, V., Gernes, D., and Szycher, M., "Advances in Electric Assist Devices", *Trans. ASAIO*, vol. XXIII, pp. 72-78, 1977.

Jarvik, R. K., Olsen, D. B., Kessler, T. R., Lawson, J., English, J., and Kolff, W. J., "Criteria for Human Total Artificial Heart Implantation Based on Steady State Animal Data", *Trans. ASAIO*, vol. XXIII, pp. 535-542, 1977.

Miller, J. A., "Artificial Organs and Beyond", *Science News*, pp. 154-156, 1977.

Szycher, M., Poirier, V., and Keiser, J., "Selection of Materials for Ventricular Assist Pump Development and Fabrication", *Trans. ASAIO*, vol. XXIII, pp. 116-124, 1977.

Tsushima, N., Kasai, S., Koshino, I., Jacobs, G., Morinaga, N., Washizu, T., Kiraly, R., and Nose, Y., "145 Days Survival of Calf with Total Artificial Heart (TAH)", *Trans. ASAIO, vol. XXIII, pp. 526-534, 1977.*

Jarvik, R. K., Nielsen, S. D., Orth, J., Summers, R. L., Isaacson, M. S., and Kolff, W. J., "Development of a Reversing Electrohydraulic Energy Converter for Left Ventricular Assist Devices", NTIS PB-290-979, 1978.

Butler, K. C., Hoffman, L. C., Moise, J. C., and Thomas, D., "Development of an Electrohydraulic Energy Converter for Left Ventricular Assist Devices", NTIS PB-300-539, 1979.

*Primary Examiner*—Ronald L. Frinks
*Attorney, Agent, or Firm*—Schuyler, Banner, Birch, McKie and Beckett

[57] ABSTRACT

A cardiac prosthesis having a hydraulically actuated compressible blood pump. An actuation chamber adjacent the blood pump receives pulses of hydraulic actuation fluid from an actuator pump through a fluid inlet path to compress the blood pump during systole and eject blood therefrom. Between pulses the actuation fluid is permitted to drain from the actuation chamber through an outlet path into a reservoir. Discharge of fluid through the outlet path is controlled by a dump valve which is adapted to close or open the outlet path primarily in response to forces which vary as a function of the flow of actuation fluid through the fluid inlet path.

56 Claims, 13 Drawing Figures

HYDRAULICALLY ACTUATED CARDIAC PROSTHESIS AND METHOD OF ACTUATION

BACKGROUND OF THE INVENTION

This invention relates to the field of cardiac prosthetic devices, and, more particularly, to hydraulically actuated total replacement artificial hearts and circulatory assist devices, including left ventricular assist devices, especially for use by and implantation in humans.

It has been estimated that between 16,000 and 50,000 patients annually are suitable candidates for implantation of a total cardiac prosthesis (TCP). Such candidates typically are disabled due to insufficient left and right ventricular function but are otherwise in good health. Many thousands more annually with inadequate left ventricular function and satisfactory right ventricular function may be candidates for a permanently implanted left ventricular assist device (LVAD).

The ideal total cardiac prosthesis must provide complete rehabilitation for the patient. Such a TCP recipient must be able to engage in gainful employment and all normal activities including moderate exercise. He should retain a substantially normal appearance and normal or near normal mobility with no significant limitations of any kind. Cardiac output effected by the TCP must be normal, adequate and sufficiently responsive to the patient's requirements to accommodate expected, sudden changes in physical activity or emotional stress level. The presence and operation of the TCP must be sufficiently unobtrusive so that the patient can largely forget that he is dependent on an artificial heart. All blood pumping functions of the TCP should be completely automatic, so that the patient performs no control or monitoring functions except for maintaining adequate power to the TCP, and responding to warnings that indicate a lack of power or serious problems requiring immediate technical or medical attention.

The intrathoracic blood pumping components of the TCP must be similar in size and weight to the natural heart. TCP life must be sufficiently long and reliability sufficiently high that risk to the patient of sudden prosthesis failure and its attendant anxiety are minimized. The formation of pannus and adherent thrombus must be prevented to avoid a compromise of blood pump function. Thrombo-emboli and excessive blood damage also must be prevented. The TCP must not damage adjacent tissues or impair organ function by toxicity and adverse tissue reactions, by mechanical trauma or compression, or by excessive local temperatures. The system must avoid skin penetrations of any kind to prevent infections that can arise from percutaneous leads. This eliminates a major risk to the patient, reduces the need for clinical observation and treatment, and reduces the maintenance of the TCP required of the patient. This ideal system must be low in cost to purchase, implant, and maintain. The frequency and extent of routine monitoring and maintenance, both medical and technical, must be low.

Serious research toward the realization of a total cardiac prosthesis has been under way since about 1957, sponsored largely by the U.S. National Institutes of Health (NIH). Researchers have directed this activity to six principal areas: (1) blood-compatible materials for the blood pumping means; (2) heart valves; (3) blood pumps; (4) blood pump actuating means; (5) power supplies and their application to the internal blood pump actuating means; and (6) control mechanisms for the pumping function.

Many materials have been developed which apparently achieve blood compatibility. See, e.g., the recent survey and evaluation of these by M. Szycher et al in "Selection of Materials for Ventricular Assist Pump Development and Fabrication", *Trans. ASAIO*, Vol. XXIII, p. 116, 1977, incorporated herein by reference. (as used herein, *Trans. ASAIO* refers to the *Transactions American Society for Artificial Internal Organs*). While there is yet no human experience, recent materials like Biomer, Avcothane, etc., have been benign (i.e., have not caused thrombo-emboli) for periods up to 221 days in the calf. The materials for blood pumping membranes or sacs, however, must not only be benign and tissue compatible, but also able to withstand tens of pounds of force for something on the order of $10^9$ flexing cycles during a 20-year prosthesis life. Apparently, appropriate materials are nearly, if not already, realized today.

Another critical element of the blood pumping means is the valves, which permit blood flow into or out of the heart, but prevent backflow of blood. Many different types of valve prostheses have been developed and used in tens of thousands of implants to replace defective natural valves. Hence, adequate valves for a TCP appear to be well within the state of the art.

There has been a great deal of development activity in the area of blood pumps, primarily associated with LVAD's. This experience has shown that by utilizing appropriate biocompatible materials as described above, adequate and reliable blood pumps can be designed. The most common form of blood pump is comprised of an elastomeric sac or diaphragm-capped cavity. In a TCP which comprises two such blood pumps, each cavity is fitted with an inlet valve and an outlet valve. These pumping cavities replicate the function of the adjacent right and left ventricles of the natural heart.

The least developed of the aforementioned areas of activity is the development of an actuator to couple the power supply to the blood pump. In order to squeeze the blood-pumping sacs or force the diaphragm into the blood pumping cavity, pneumatic actuation means supplied from outside the body are most common. A number of mechanical actuation systems may be found in the literature. All sorts of linkages, gears, cams, etc., have been proposed, but none is known to be successful. Most of these systems are driven by an electric motor, although some have relied upon piezoelectric devices and other esoteric means. Both copulsation, the technique used by the natural heart, and alternate pulsation of left and right ventricles have been employed successfully. See Smith, L. M.; Olson, D. B., Sandquist, G., Grandall, E., Gentry, S., and Kolff, W. J., "A Totally Implantable Mechanical Heart", *Proceedings from the European Society of Artificial Organs*, Vol. 2, p. 150, 1975. Medical opinion appears to be impartial regarding this choice.

The coupling of a mechanical drive to the sensitive blood pumping diaphragm or sac is difficult to accomplish without raising excessive stresses and causing fatigue failures. Hence, the preferred coupling means is fluid, either liquid or gas. For example, one group has constructed an electric motor powered, cam-actuated, diaphragm air pump which couples to the blood-pumping sac via pneumatic pressure. See V. Poirier et al., "Advances in Electrical Assist Devices," *Trans. ASAIO*, Vol. XXIII, p. 72, 1977, incorporated herein by reference. The entirety of the above-described mechanism is intended to be implanted within the thoracic cavity. In the Poirier et al design the motor rotates only once per heartbeat. Because relatively large torque is required from the motor, it must use strong magnetic fields, employ high current, and is rather heavy.

Burns et al, by contrast, constructed a TCP actuation system using a 10 k-40 k rpm motor driving a hydraulic pump pressurizing a liquid to actuate the blood-pumping bladders. See W. H. Burns et al., "The Totally Implantable Mechanical Heart, an Appraisal of Feasibility," *Annals of Surgery*, Sept. 1966, pp. 445-456, and W. H. Burns et al., "The Total Mechanical Cardiac Substitute," *Process in Cardiovascular Diseases*, Vol. XII, No. 3, 1969, pp. 302-311, both incorporated herein by reference. However, the electromechanically actuated hydraulic switching valve used in this and similar systems to shunt hydraulic fluid back and forth between ventricular actuating chambers has a number of disadvantages. The switching valve itself is relatively large and heavy, consumes a great deal of power and is potentially unreliable. Long and large ducts required in this type of system cause undesirable large frictional and inertial losses, and long fluid acceleration times.

Another approach to hydraulic actuation taken by researchers has involved the use of a reversible pump which directly pumps fluid back and forth between the two actuating chambers. See Jarvik U.S. Pat. No. 4,173,796.

On the subject of power, up to this time most TCPs implanted in the calf have been powered pneumatically via transcutaneous tubing into the thoracic cavity. A large external console supplies the proper regimen of pressure variations in order to activate the internal blood pump. With such a system, calves have lived up to 221 days. Jarvik, "The Total Artificial Heart", *Scientific American*, Vol. 244, No. 1, pp. 74-80, January, 1981. On another tack, NIH has sponsored considerable effort on the development of internal nuclear power supplies and, to a lesser extent, of chemical fuel cells. None of this work, however, appears to be promising; in fact, the nuclear effort was terminated by the U.S. Energy Research and Development Administration. Additionally, various means of transmitting mechanical power transcutaneously have been attempted, but none appears to be promising. At present, transcutaneous transmission of electricity appears to be the preferred method for powering a TCP. A second, less preferable, possibility is the supplying of electrical power through percutaneous wire penetrations, but these always pose a threat of infection and are psychologically annoying to the patient.

Several investigators have developed the technique of transcutaneous electrical power transmission. Their approach is to implant a coil under the skin. This coil functions as a transformer secondary winding, receiving power from an inductively coupled, external, mating coil juxtaposed therewith to serve as the transformer primary winding. At frequencies on the order of 17 kHz, up to 100 watts have been thus transmitted for many months across the skin of a dog, by Schuder. See, J. C. Schuder et al., "Ultra High Power Electromagnetic Energy Transport Into the Body," *Trans. ASAIO*, 1971, incorporated herein by reference. Thus, it appears that the inductive delivery across the intact skin of the approximately 30 watts needed to power a TCP is well within the state of the art.

On the subject of control of a TCP to make it sympathetic to the body, there have been many different approaches and much controversy. Some researchers have attempted to provide no active control. Others have required a control in order to achieve regular beating. See, e.g., W. H. Burns et al, "The Total Mechanical Cardiac Substitute," identified above. Some systems have attempted to control systole (i.e., the contraction phase of the cardiac cycle whose rate is one determinant of cardiac output) from the left ventricle of the TCP in order to control the systolic pressure in the aorta. Still other systems have attempted feedback control of stroke volume and beat rate.

The natural heart and at least some, if not all, TCPs are comprised of two pumps in series. The right pump receives blood from the vena cava and impels it into the pulmonary artery. The left pump receives blood from the pulmonary vein and impels blood into the main circulatory system via the aorta. These two pumps must, over time periods considerably longer than that of a few beats, pump nearly the same amount of blood. Otherwise, the delicate pulmonary circuit will either collapse or rupture from a deficiency or excess of blood pumped by the right ventricle relative to the left. Various investigators have included controls in their TCP systems in order to achieve the critical balance between the pumping rate of the right and left ventricles. The major intrinsic mechanism by which the natural heart controls cardiac output is described by Starling's Law, which essentially states that a ventricle will expel during systole essentially that blood which flows into the relaxed ventricle during diastole. For the right ventricle, the body controls the "tone", i.e., the pressure in the venous system, so that the pressure in the vena cava (relative to atmospheric pressure) may rise from 5 to 15 mm Hg when there is a demand for higher blood flow. This pressure change causes approximately a proportional increase in the amount of blood which flows from the vena cava through the tricuspid valve into the relaxed right ventricle during diastole.

It is important to note that the natural heart has no means to suck upon the veins. It can only produce a systolic contraction which expels blood from the ventricular chamber.

Similarly, for the left ventricle, the pressure in the pulmonary vein varies from 5 to 15 mm Hg and produces a proportional increase in blood flow into the left ventricle. If the right ventricle should temporarily pump slightly more than the left ventricle, the pressure rises in the pulmonary artery, and, as a consequence, in the pulmonary vein, causing more blood to flow into the left ventricle and thereby matching the pumping rate of the left ventricle to that of the right ventricle. Thus, the natural heart achieves the necessary balance between the two pumps in series via simple and direct fluid dynamic means. In a real sense, the heart is the servant, not the master of the circulatory system, and in particular it responds in the final analysis to the requirements of the body as reflected by the peripheral oxygen saturation. The above-described intrinsic control can maintain body function even in the absence of extrinsic humoral or neural control.

The body also neurally controls the rate at which the natural heart beats. Cardiac output is a function of the amount of blood ejected during systole, and the rate at which the heart beats. For all but the most strenuous activity, the systolic stroke volume per beat remains substantially constant. Thus, cardiac output is primarily a function of beat rate (i.e., the number of beats per minute). Heart rates can vary from a low of about 40 to as high as 220 beats per minute in a young person and ordinarily from about 60 to 150 bpm in an adult. Cardiac output of the natural heart can vary from about 4 to as high as 24 liters per minute, the latter being the case of a trained athlete. Experience with pacemakers and transplanted natural hearts shows that beat rate control via neural sensors is unnecessary for a satisfactory life. The hundreds of natural hearts which have been transplanted operate at their own beat frequency, unresponsive to the body's neural demands because there is no neural connection.

The natural control system also ensures that the systolic pressure in the aorta does not drop below about 80 mm Hg, in order to maintain adequate circulation to the brain. The mean pressure in the aorta is established by cardiac output and the peripheral resistance of the vascular systems. In some of the TCPs which previously have been developed, a control means has been provided to maintain pressure in the aorta and atrium within a reasonable range. On the other hand, there is evidence from natural heart transplants that such control is unnecessary; transplanted human hearts have no neural connections to the host body and hence their systolic rates are not related to neural control, yet people with such transplants have been able to lead meaningful lives. It may be concluded that a TCP can be satisfactorily operated without such control. The evidence above teaches that a workable TCP can be made to approximate the natural heart's Starling's Law behavior with relatively simple control operations.

Thus, a TCP is now technically feasible provided that a competent design is constructed. The critical blood pumping technology appears to be well established and adequate for long-term survival of the recipient. Benign power transmission across the skin can obviate the portent of infection of the thoracic cavity transmitted via percutaneous leads. One major area where satisfactory progress is lacking, however, is the provision of a practical blood pump actuating mechanism. What is needed is a simple, lightweight, reliable, transcutaneously supplied, electrically-driven actuator. This objective is the one to which the present invention is principally addressed.

SUMMARY OF THE INVENTION

Accordingly, it is an object of the present invention to provide a hydraulic actuation system for use in TCPs and circulatory assist devices which obviates many of the drawbacks of the prior art actuation systems.

More specifically, it is an object of this invention to provide a simple and reliable hydraulically actuated cardiac prosthesis, especially a TCP.

Another object of the invention is to provide a total cardiac prosthesis which is substantially unobtrusive and permits the patient to engage in all normal activities, without significant limitations of any kind.

Another object of the invention is to provide a total cardiac prosthesis wherein all blood pumping functions are completely automatic, and wherein minimum patient attention is required to maintain prosthesis operation.

Another object of the invention is to provide a total cardiac prosthesis which permits monitoring of mechanical and physiological information and which is provided with alarms to warn of power failures or other malfunctions.

Another object of the invention is to provide a total cardiac prosthesis which obeys Starling's Law.

These and other objects of the present invention are accomplished in the most basic form of this invention by providing an implantable hydraulic actuation system for supplying motive power to a blood pumping chamber having a flexible portion, comprising an actuation fluid reservoir; actuation fluid pumping means in fluid communication with the reservoir for providing intermittent pulses of actuation fluid; an actuation chamber having an actuation fluid inlet path in fluid communication with the pumping means, and a separate actuation fluid outlet path in fluid communication with the reservoir; the actuation chamber being adapted to cause displacement of the flexible portion of the blood pumping chamber in response to changes in volume of actuation fluid in the actuation chamber; and valve means associated with the actuation chamber adapted to close or open the actuation fluid outlet path primarily in response to forces which vary as a function of actuation fluid flow through the actuation fluid inlet path.

The present invention also is directed to an implantable hydraulically actuated blood pumping system comprising a blood pumping chamber having a blood inlet, a blood outlet and a flexible portion; an actuation fluid reservoir; actuation fluid pumping means in fluid communication with the reservoir for providing intermittent pulses of actuation fluid; an actuation chamber having an actuation fluid inlet path in fluid communication with the pumping means, and a separate actuation fluid outlet path in fluid communication with the reservoir, the actuation chamber being operatively associated with the blood pumping chamber to cause displacement of the flexible portion of the blood pumping chamber in response to changes in volume of actuation fluid in the actuation chamber; and valve means associated with the actuation chamber adapted to close or open the actuation fluid outlet path primarily in response to forces which vary as a function of actuation fluid flow through the actuation fluid inlet path whereby the actuation chamber fills with actuation fluid and blood is expelled from the associated blood pumping chamber while the valve means is closed, and actuation fluid drains from the actuation chamber and the associated blood pumping chamber is allowed to fill with blood while the valve means is open.

The present invention also provides an implantable hydraulically actuated total cardiac prosthesis comprising a pair of blood pumping chambers each having a blood inlet, a blood outlet and a flexible portion; a pair of actuation chambers each having an actuation fluid inlet path and a separate actuation fluid outlet path, one of the actuation chambers being operatively associated with one of the blood pumping chambers and the other of the actuation chambers being operatively associated with the other of the blood pumping chambers to cause displacement of the flexible portion of the blood pumping chambers in response to changes in volume of actuation fluid in their associated actuation chambers; an actuation fluid reservoir in fluid communication with the actuation fluid outlet paths; actuation fluid pumping means in fluid communication with the reservoir and the actuation fluid inlet paths for providing intermittent pulses of actuation fluid from the reservoir to the actuation chambers; and valve means associated with the actuation chambers adapted to close or open the actuation fluid outlet paths primarily in response to forces which vary as a function of actuation fluid flow through the associated fluid inlet path whereby the actuation chamber fills with actuation fluid and blood is expelled from the associated blood pumping chamber while the valve means is closed, and actuation fluid drains from the actuation chamber and the associated blood pumping chamber is allowed to fill with blood while the valve means is open.

The present invention also includes a method of actuating an implantable blood pump comprising a blood pumping chamber having a blood inlet, a blood outlet, and a flexible portion, and an actuation chamber operatively associated with the blood pumping chamber having an actuation fluid inlet path, an actuation fluid outlet path and valve means associated with the actuation fluid outlet path, comprising the steps of delivering intermittent pulses of actuation fluid to the actuation chamber through the actuation fluid inlet path; and alternately closing and opening the actuation fluid outlet path with the valve means in response to forces which vary as a function of actuation fluid flow through the actuation fluid inlet path to cause the actuation chamber to fill with actuation fluid and blood to be expelled from the blood pumping chamber while the valve means is closed and to cause the actuation fluid to drain from the actuation chamber and blood to fill the blood pumping chamber while the valve means is open.

The present invention further contemplates a method of actuating an implantable blood pump comprising a blood pumping chamber having a blood inlet, a blood outlet, and a flexible portion and an actuation chamber operatively associated with the blood pumping chamber having an actuation fluid inlet path, an actuation fluid outlet path and valve means associated with the actuation fluid outlet, comprising the steps of delivering intermittent pulses of actuation fluid to the actuation chamber through the actuation fluid inlet path; closing the actuation fluid outlet path with the valve means at the beginning of each fluid pulse, by supplying sufficient flow of actuation fluid through the inlet path to create forces on the valve means above a predetermined threshold magnitude; maintaining the actuation fluid outlet path closed with the valve means during each fluid pulse by continuing to supply sufficient flow of actuation fluid through the inlet path to maintain said forces at or above the predetermined threshold magnitude, to cause the actuation chamber to fill with actuation fluid and blood to be expelled from the blood pumping chamber during the fluid pulse; and opening the actuation fluid outlet path with the valve means at the end of each fluid pulse by reducing the flow of actuation fluid through the inlet path to cause said forces to fall below the predetermined threshold magnitude, to cause the actuation fluid to drain from the actuation chamber and blood to fill the blood pumping chamber between the fluid pulses.

The present invention also is directed to a method for actuating a total cardiac prosthesis based on the above-described method of actuating an implantable blood pump.

BRIEF DESCRIPTION OF THE DRAWINGS

The novel features of the invention are set out with particularity in the appended claims, but the invention will be understood more fully and clearly from the following detailed description of the invention as set forth in the accompanying drawings, in which:

DETAILED DESCRIPTION

The present invention is based at least in part on the discovery of a new approach to the controlled hydraulic actuation of a blood pump for use in cardiac prostheses. This actuation method and the various mechanical forms suitable for practicing it can be used with equal facility in total cardiac prostheses and circulatory assist devices. Since the similarities of structure and operation of these two classes of devices are well known in the art, the following description of this invention will relate primarily to the hydraulically actuated TCP.

THE TCP SYSTEM

Figure 1:
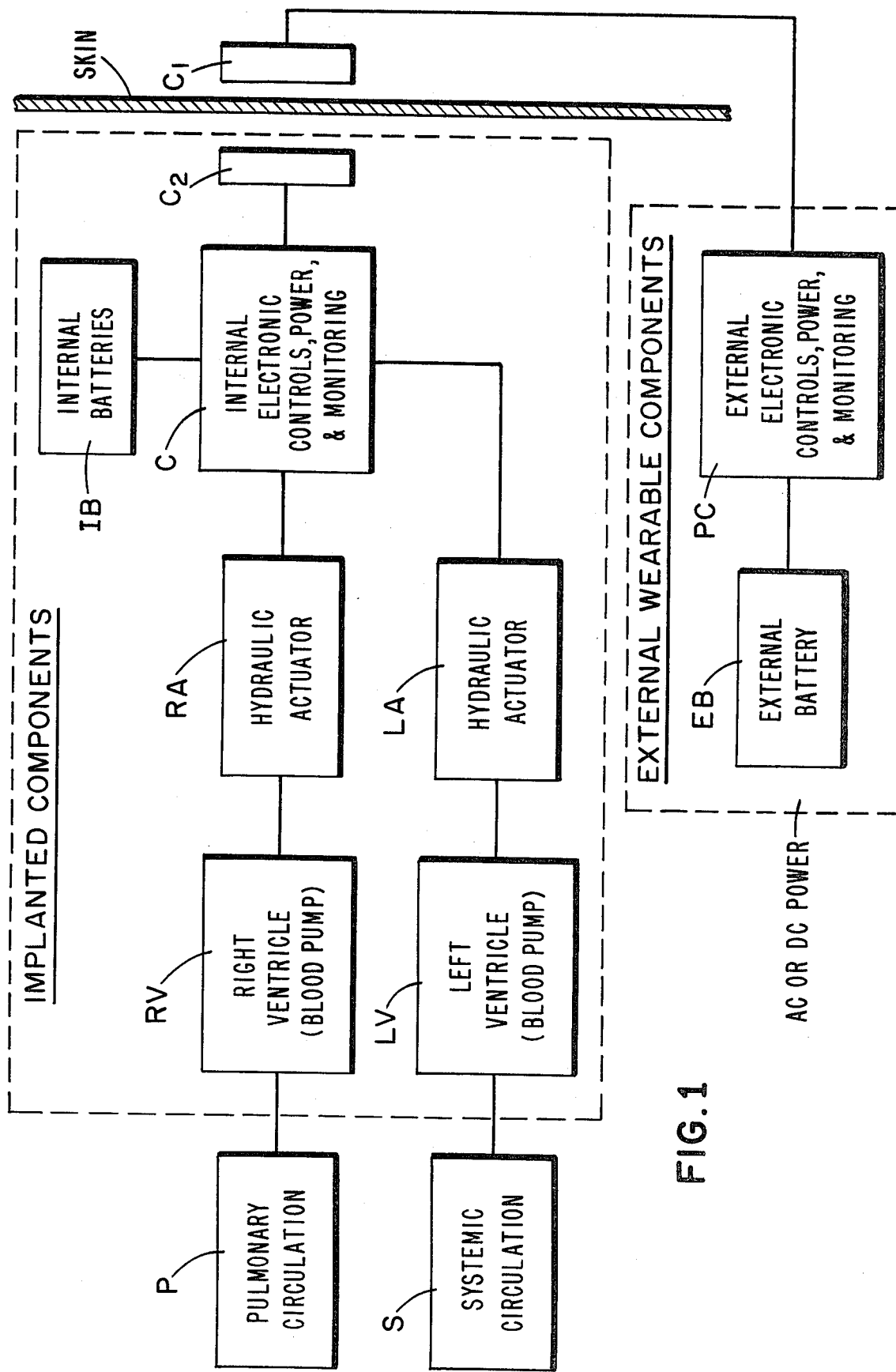
FIG. 1 is a block diagram showing the major components of a total cardiac prosthesis system according to the present invention.

FIG. 1 schematically illustrates the basic components of a TCP system according to the invention and the interaction of these components with the physiological systems of the patient. The pulmonary circulation P is maintained by a right ventricular blood pump RV. The systemic circulation S is maintained by a left ventricular blood pump LV. In the preferred embodiment of this invention each of the ventricular blood pumps is powered by a separate hydraulic actuator, RA for the right blood pump and LA for the left blood pump. The operation of the actuators RA and LA is controlled and monitored by an internal electronic control, power and monitoring circuit C which is powered at times by internal batteries IB. Most of the time, however, power is derived from an external power supply comprising an external battery EB and power circuit PC. External battery EB is rechargeable from a conventional power supply, such as household AC current or automotive DC current. Power is delivered transcutaneously to the implanted components by magnetic induction from a primary coil $C_1$ to a secondary coil $C_2$.

Preferably, the blood pumps and actuators are implanted within the thoracic cavity, while the internal electronic controls C and internal batteries IB are implanted outside of the thoracic cavity, preferably near the skin so as to permit easy replacement or servicing of these components by minor surgery. Of course, secondary coil $C_2$ must be located close to the skin for efficient inductive energy transfer.

BLOOD PUMPS

The blood pumps of the TCP system according to this invention have essentially the same size, configuration and function as the natural heart. These functions include the same stroke volume capability, the same beat rate range, the same atrial filling pressure range and the same arterial pressure range and profile as in a healthy heart.

Blood pumps suitable for use according to the present invention can be of any of the known designs which are capable of being actuated by hydraulic actuation systems. This class includes systems in which the actuation fluid does work directly on a component of the blood pump as well as those systems in which the hydraulic fluid is coupled to the blood pump by indirect means, such as by magnetic coupling. Of primary interest, however, are those blood pump types in which the hydraulic fluid acts directly on a flexible portion of the blood pump. Examples of this type of blood pump include sac-type and membrane-capped cavity types generally known in the art. The preferred blood pumps for use in the TCP of this invention are of the membrane type (sometimes called bladder-type).

These preferred blood pumps essentially comprise a ventricular chamber containing blood inflow and outflow valves. The right and left ventricular blood pumps are generally of the same design except that the housings contain inflow and outflow ducts with orientations necessary to achieve appropriate implantability and fit.

Figure 2:
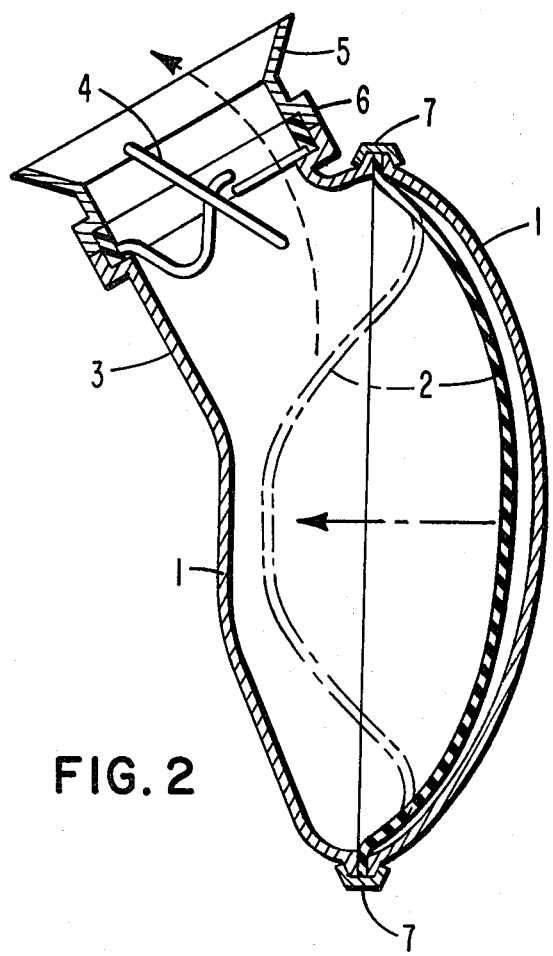
FIG. 2 is a sectional view of one type of blood pump suitable for use in a TCP according to the present invention.
Figure 13:
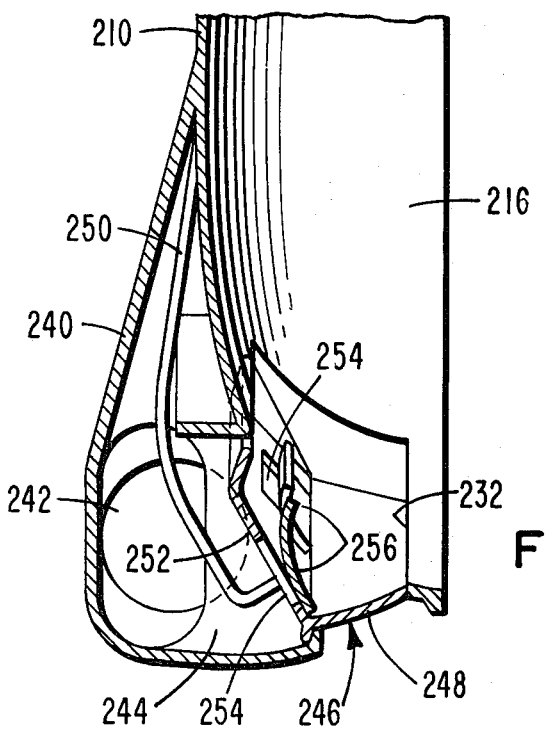
FIG. 13 is a view similar to FIG. 12, but showing the dump valve in its closed position.
Figure 12:
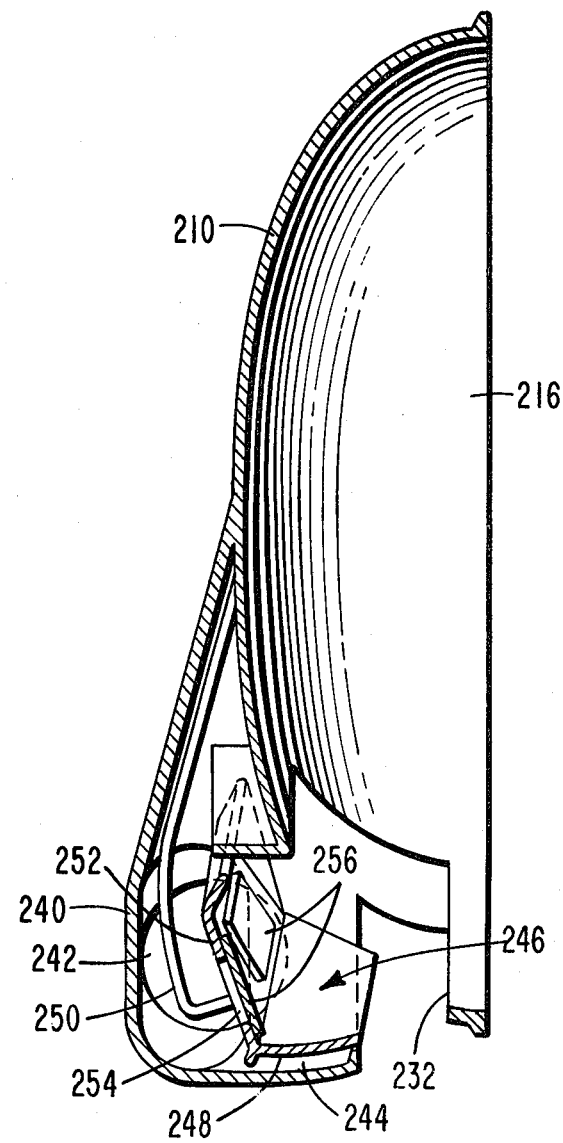
FIG. 12 is a sectional view of the structure shown in FIG. 9 taken along line 12—12 of FIG. 10, and showing the dump valve in its open position.

One preferred form of blood pump is schematically illustrated in FIG. 2. The blood pump includes a two-piece rigid housing 1 in which is mounted a flexible membrane, or bladder 2, which is fabricated from an elastomeric material. The housing parts 1 and bladder 2 are secured together at their peripheries by a clamping ring 7. As the blood pump fills with blood during diastole, the flexible membrane assumes the position shown in FIG. 2 in solid lines. As hydraulic fluid is added to the housing on the non-blood side of the membrane (in a manner later described), the change in hydraulic fluid volume causes displacement of the membrane to the position shown in dotted lines. As the membrane is displaced toward the opposite housing wall, blood is forcibly expelled from the blood pump. The membrane should be of such a design that the displacement or deformation occurs uniformly and consistently with each flexing stroke. The membrane also should be designed to intrinsically avoid blood damaging contact with any portion of the rigid housing, and/or extrinsic control means should be provided to so limit the excursion of the membrane.

The blood pumping chamber is provided with a blood outflow duct 3 containing a suitable prosthetic outflow valve device 4. An inflow duct (not shown) with a suitable prosthetic inflow valve also is provided.

An example of suitable mechanical prosthetic valves are Bjork-Shiley valves although numerous other designs also may be employed. The blood pump inflow and outflow tracts preferably are connected respectively to known types of atrial cuffs 5 and arterial grafts (not shown) by snap-on quick-connect fittings 6 of any suitable design which facilitate surgical implantation of the TCP. The cuffs and grafts preferably are anastomosed to the atrial remanent and the aorta or pulmonary artery before the blood pumps are connected thereto.

The blood pumping membrane 2 preferably is of the single layer type formed from a high strength elastomeric biocompatible material. Polyurethane-based polymers such as Biomer and Avcothane are among the suitable materials for this application. These types of materials have been shown to exhibit high endurance and reliability in blood pumping operations. It is also important that the membrane of the blood pump exhibit low adhesion of thrombus and low generation of thrombo-emboli. The housing is formed of a suitable rigid metallic or plastic material, such as stainless steel coated with polyurethane or other biocompatible coatings, or glass or carbon fiber reinforced plastic. Typically, all internal surfaces of the blood pumps are coated with a suitable biocompatible material.

A suitable blood pump for use in the TCP of the present invention should be capable of providing a range of cardiac outputs of from 2.8 to about 9.5 liters per minute employing full stroke volume and at a beat rate of from about 35 to 120 beats per minute.

ACTUATION SYSTEM

In the TCP of the present invention, the above-described blood pumps are hydraulically actuated. While any incompressible fluid which is compatible with the actuator system components can be employed, the preferred actuation fluid is physiologic saline solution (0.9 g percent NaCl) which is very close in saline composition to blood plasma. The use of saline as an actuation fluid promotes osmotic equilibrium and permits maintenance of a fixed actuation fluid inventory. It also eliminates the problems associated with the use of certain other actuation fluids such as silicone oils, including diffusion of these oils into the body or diffusion and mixing of body fluids into the actuation fluid which can cause degradation of the polymer materials in the flexible membrane.

The actuation system of the present invention in its most basic form comprises four basic components: (1) an actuation fluid reservoir or compliance sac, (2) actuation fluid pumping means, (3) a ventricular actuation chamber and (4) a flow responsive ventricular dump valve. The basic manner of operation of this system involves the pumping of actuation fluid pulses from the actuation reservoir into the ventricular actuation chamber to displace the flexible blood pump membrane and expel blood from the pump. The ventricular dump valve, which operates in response to actuation fluid flow into the actuation chamber, serves both to close off the actuation chamber outlet during each fluid pulse and to drain or dump the actuation chamber fluid inventory at the end of each pulse, which permits refilling of the blood pumping chamber.

Figure 3:
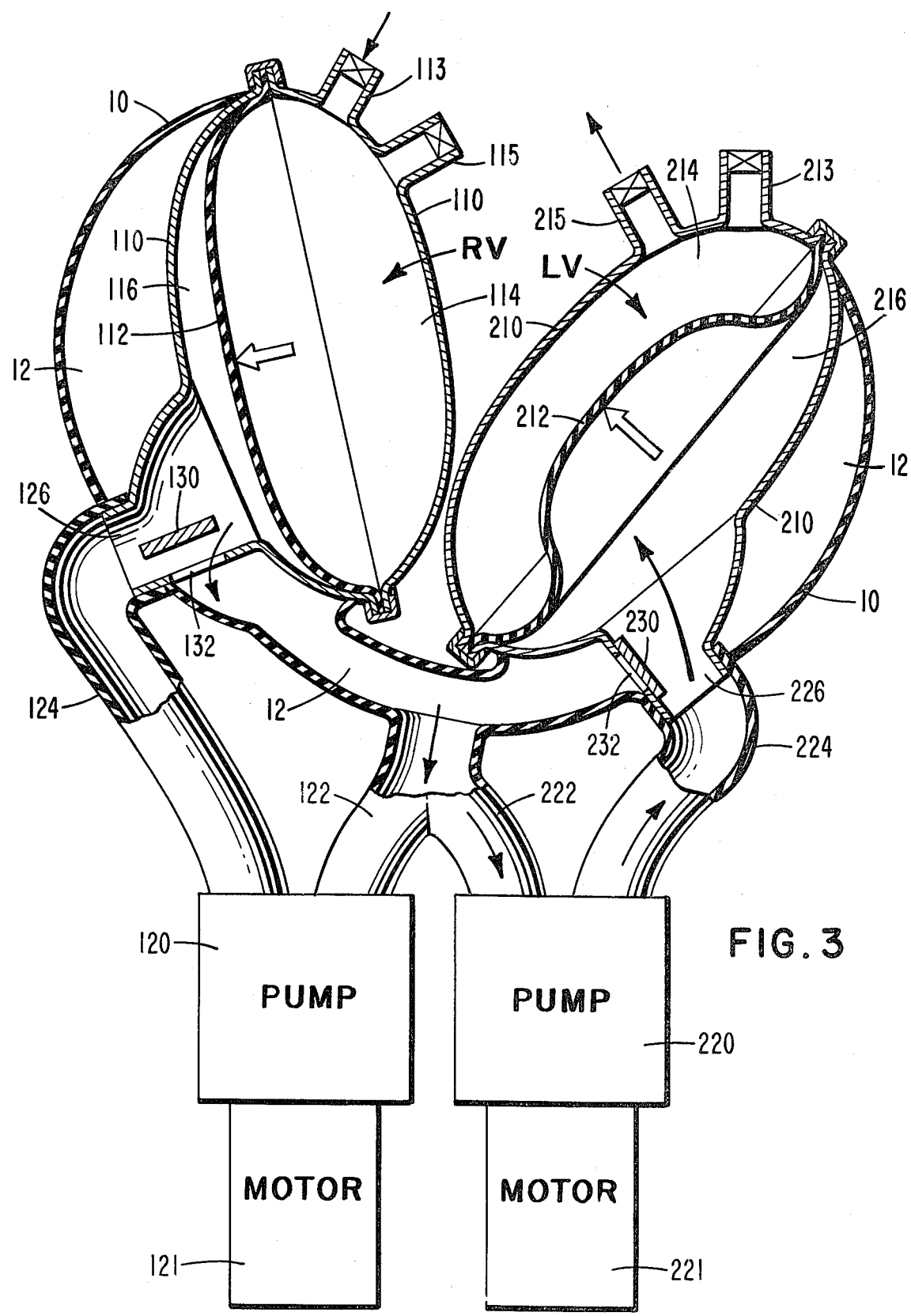
FIG. 3 is a schematic illustration of one embodiment of a total cardiac prosthesis actuation scheme according to the invention.

FIG. 3 schematically illustrates a preferred actuation system for the TCP of the invention. The blood pumps include a right ventricle RV and a left ventricle LV. Right ventricle RV is defined by a rigid housing 110 which is divided by a flexible bladder 112 into a blood pumping chamber 114 and a fluid actuation chamber 116. Similarly, left ventricle LV is defined by a rigid housing 210 which is divided by a flexible bladder 212 into a blood pumping chamber 214 and a fluid actuation chamber 216. Valved blood inlets 113, 213 and valved blood outlets 115, 215 interconnect the blood pumping chambers 114, 214 with the appropriate blood vessels.

Portions of the blood pump housings 110 and 210 are surrounded by a flexible membrane 10 which defines a fluid containing reservoir or compliance sac 12. This compliance sac faces the lung and other soft tissues in the thoracic cavity and contains actuation fluid maintained at normal intrathoracic pressure levels. During operation, the fluid is dumped from each ventricle into the compliance sac during diastole and is removed from the compliance sac during systole. In the preferred form of operation, the ventricles are alternately actuated so as to minimize the change in volume of hydraulic actuation fluid in the system and therefore the overall size of the compliance sac. Copulsatile operation can, of course, be effected if desired.

In the preferred embodiment of FIG. 3, each of the blood pumps is independently actuated by its own pumping means which preferably comprises a high speed, mixed flow, rotary pump driven by a brushless DC motor, although other suitable motor and pump designs may, of course, be used. The pump and motor bearings are totally immersed in and lubricated by the saline actuation fluid. In the preferred embodiment this hydraulic pump is designed to operate at a speed of about 7,000 to 15,000 rpm during the ventricular ejection phase (systole). To effect diastole the pump can be stopped, but it is preferred to provide a pump which can be slowed to about 1,000 to 1,200 rpm. At this low speed the pump will provide insufficient flow to actuate the flow responsive dump valve (described below), yet will maintain a full lubricating fluid film on the bearings.

The operation of the electric motor which drives the hydraulic pumps is continuously controlled in a manner hereinafter described, preferably using back emf commutation of the type described in Chambers et al, "Development of an Electrical Energy Converter for Circulatory Devices," NTIS Publication No. PB-245 042, May, 1975, incorporated herein by reference.

Referring to FIG. 3, actuation pump 120, driven by motor 121, draws fluid from compliance sac 12 through a flexible duct 122 and delivers it to actuation chamber 116 via a flexible duct 124 through inlet 126. Similarly, actuating pump 220 driven by motor 221 draws fluid from compliance sac 12 through a flexible duct 222 and delivers it to actuation chamber 216 via flexible duct 224 through inlet 226. As indicated above, each hydraulic pump is started and operated during systole of its corresponding ventricle and stopped or slowed during diastole of that ventricle.

The actuation chamber is also provided with flow responsive ventricular dump valve means to effect dumping of hydraulic fluid from the actuation chamber at the end of systole. The term "flow responsive" in intended to include those valves which open and close the actuation chamber outlet primarily in response to forces which vary as a function of actuation fluid flow into the actuation chamber. Typically, this flow responsive mechanism will act in response to the pressure or momentum forces created by the incoming actuation fluid or to some combination of these forces. Such a flow actuated valve typically is provided with a threshold bias toward the open position. Accordingly, the valve closes only after the flow associated forces created during initial flow into the actuation chamber exceed this threshold. As long as the forces created by flow of actuation fluid into the actuation chamber are above this threshold, the valve will remain closed—i.e., throughout the systolic phase. When the flow of actuation fluid is stopped or reduced below the threshold bias forces, the bias returns the valve to its open position thereby dumping the actuation fluid from the chamber—i.e., the diastolic phase.

Referring again to the schmatica representation in FIG. 3, flow responsive valves 130, 230 are provided adjacent inlets 125, 226, respectively, for controlling the outflow of actuation fluid from actuating chambers 116, 216 into compliance sac 12 through outlets 132, 232. In the operational state shown in FIG. 3, pump 220 is delivering actuator fluid to actuating chamber 216 through inlet 226. This inflow has caused valve 230 to close outlet 232, thereby preventing the escape of actuator fluid from actuating chamber 216. As pump 220 continues to operate, the volume of fluid within actuating chamber 216 increases, thereby compressing blood pumping chamber 214 and forcing blood outwardly therefrom through outlet 215 into the systemic vasculature. At the same time, pump 120 is not actively pumping actuation fluid to actuating chamber 116 through inlet 126. Hence, valve 130 remains in its open position, thereby allowing actuation fluid to drain from actuating chamber 116 into compliance sac 12. This drain of actuating fluid is caused by the right atrial blood pressure, which forces blood into the right ventricular blood pumping chamber 114 through inlet 113. Filling of each blood pumping chamber is therefore passive, as in the natural heart. When pump 120 is activated and pump 220 turned off or slowed down, the left ventricle is permitted to fill, while the right ventricle is compressed to eject blood into the pulmonary system through outlet 115. Of course, the pumps could be operated in copulsatile fashion, as long as a sufficient quantity of actuation fluid is present.

Figure 4:
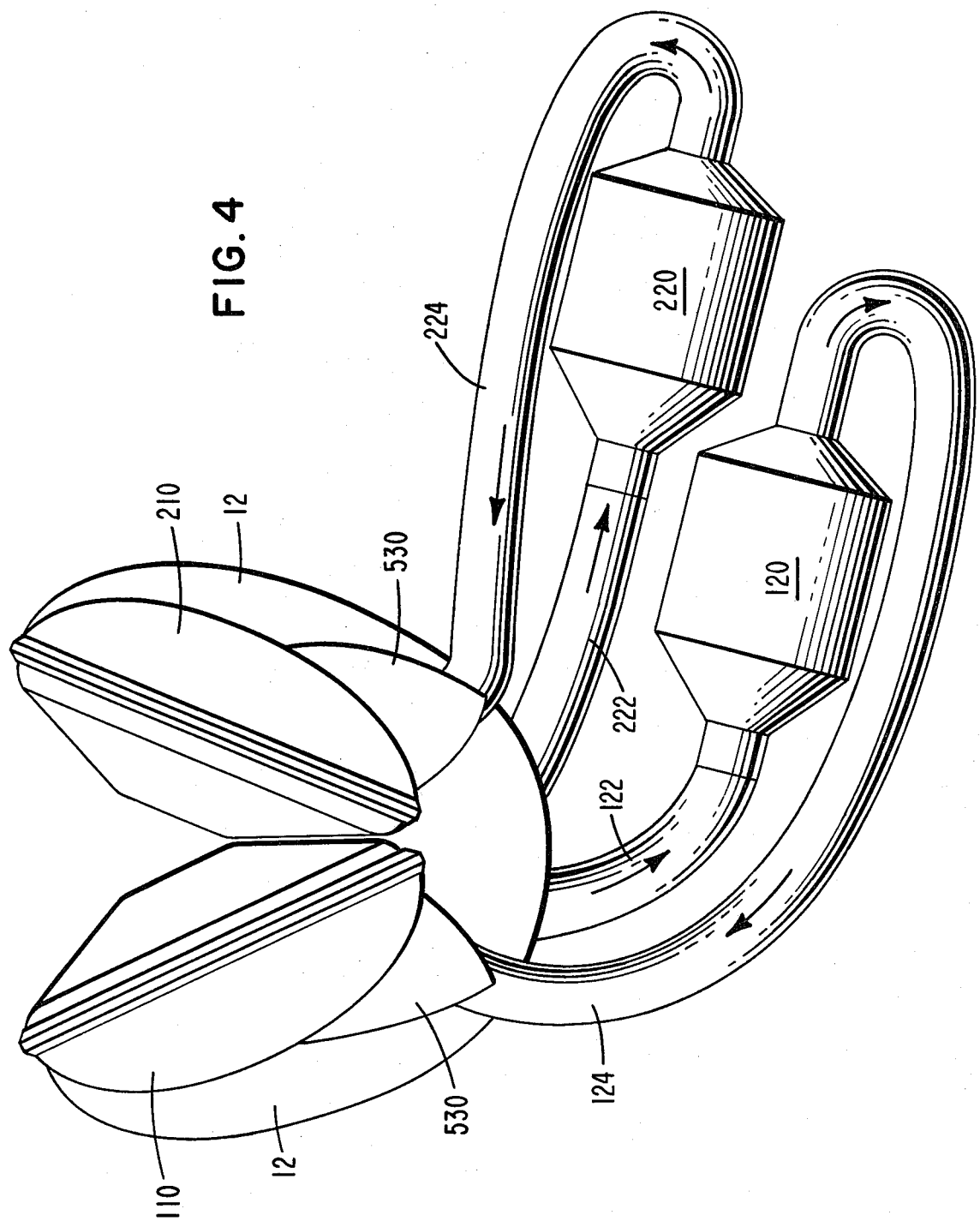
FIG. 4 is a perspective view of one form of the TCP actuation scheme illustrated in FIG. 3.

FIG. 4 illustrates a preferred mechanical configuration for the actuation system embodiment shown schematically in FIG. 3. Flow actuated dump valves 530 are integrally formed on ventricle housings 110, 210. Flexible conduits 122, 124, 222, 224 connect the pumps 120, 220 to dump valves 530 and the compliance sac 12.

Utilization of the above-described preferred embodiment provides a number of significant advantages. Utilization of two independent actuation systems allows for independent ventricular control as well as pump and motor optimization for each ventricle to maximize efficiency. Moreover, the use of flow actuated dump valves provides for the elimination of valve electromechanical actuators and thereby improves the reliability of the resulting TCP.

Figure 5:
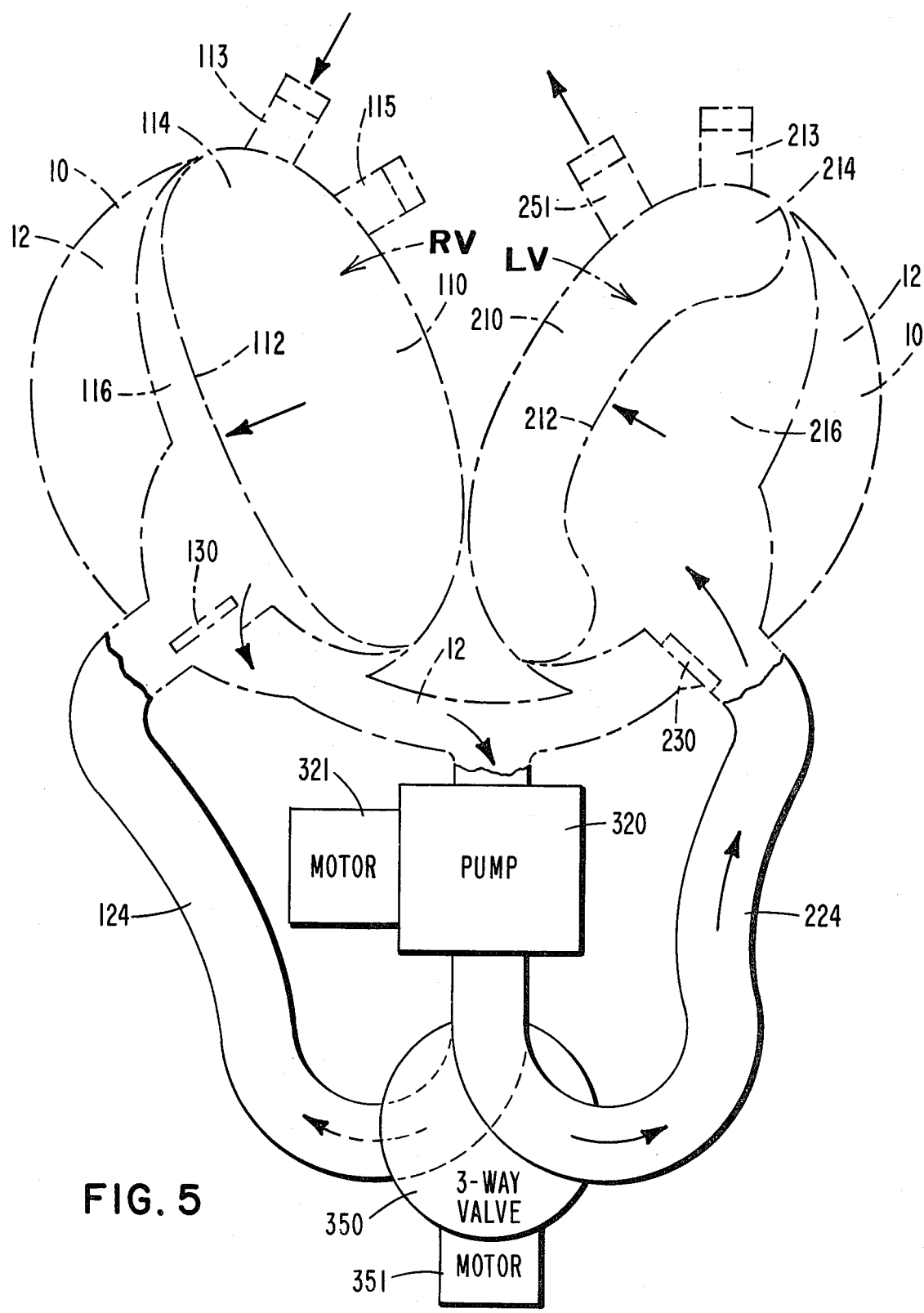
FIG. 5 is a schematic illustration of another embodiment of a total cardiac prosthesis actuation scheme according to the invention.

FIG. 5 schematically illustrates an alternative embodiment in which the portion shown in dot-dash lines is identical to the corresponding portion of the embodiment shown in FIG. 3. In this embodiment a single actuator pump 320 is driven by motor 321. An electromagnetically operated three-way switching valve 350, driven by motor 351, alternately diverts actuation fluid from the pump outlet to actuating chambers 116, 216 through flexible ducts 124, 224 in response to signals from the control circuit to provide alternate pulses of actuation fluid to the actuation chambers. If copulsatile operation is desired, valve 350 and motor 351 can be eliminated. Flow responsive dump valves 130, 230 used in this system are the same as those described generally above in connection with FIG. 3.

Figure 6:
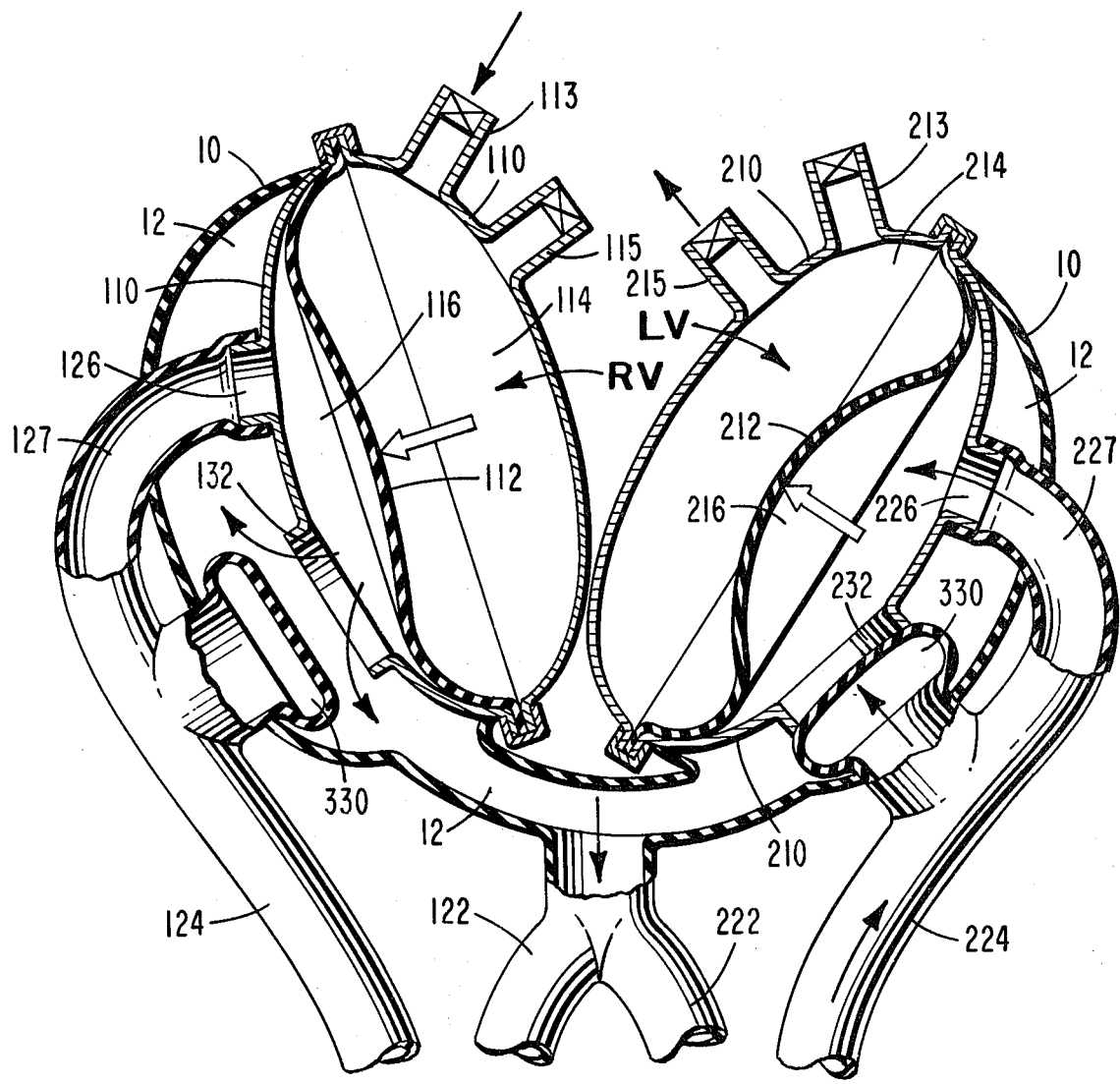
FIG. 6 is a schematic illustration of a portion of a TCP according to the invention showing one embodiment of a flow responsive ventricular dump valve for controlling the flow of actuation fluid out of each actuation chamber.

FIG. 6 schematically illustrates one type of flow responsive dump valve useful according to the present invention. Each valve comprises an expandable mushroom shaped bladder 330. Bladders of other suitable shape may also be used. Bladder 330 may be made of an elastomeric material having a natural resiliency, or of a suitable flexible, non-elastic material. Bladders 330 expand against outlets 132, 232 of the actuation chambers when filled with pressurized actuation fluid delivered by actuator pumps 120, 220. Fluid inlets 126, 226 comprise branch conduits 127, 227. Outlet 232 is shown closed by valve 330, actuation fluid continuing past valve 330 into actuating chamber 216 through conduit 227. Outlet 132, on the other hand, is open. Either the natural resiliency of the elastomeric material, and/or a spring (not shown), may be employed to cause the bladder to return to the retracted (open) position.

Figure 7:
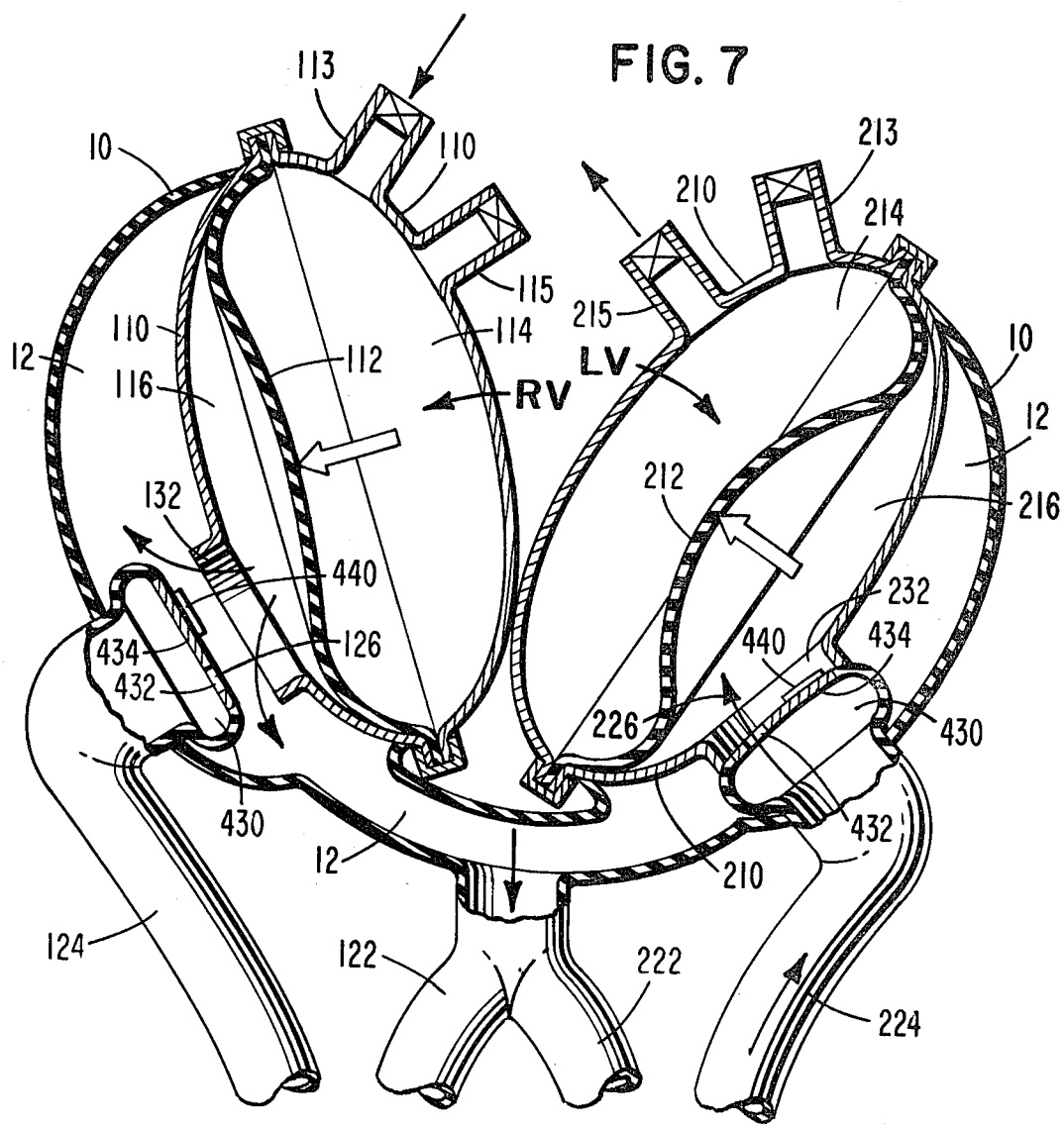
FIG. 7 is a view similar to FIG. 6 illustrating another embodiment of a flow responsive ventricular dump valve.
Figure 8:
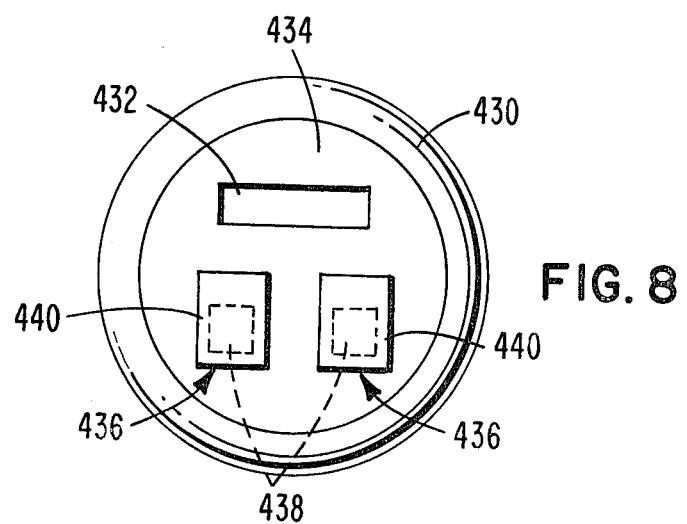
FIG. 8 is a detail view of one form of the dump valve used in the embodiment of FIG. 7.

FIGS. 7 and 8 illustrate another embodiment of a flow responsive dump valve of the expandable bladder type used in both right and left ventricles. The valve will be described in connection with the left ventricle. The valve similarly comprises an expandable mushroom shaped bladder 430 which expands against outlet 232 of actuating chamber 216 when filled with actuation fluid delivered by actuator pump 220. Either the natural resiliency of the elastomeric material and/or a spring (not shown) may be employed to bias the bladder to its retracted (open) position.

In contrast to the embodiment of FIG. 6, fluid inlet 226 comprises at least one orifice 432 in the cap of bladder 430. The cap comprises a substantially rigid wall portion 434 which can be formed of a suitable metallic or plastic material. In operation, when actuator pump 220 delivers actuating fluid to bladder 430, the fluid flows into actuation chamber 216 through orifice 432. Orifice 432 restricts the flow of actuation fluid sufficiently to cause the fluid pressure within bladder 430 to increase. When a sufficient pressure differential across cap 434 has developed to overcome the bladder's bias, the bladder is forced to expand against and close outlet 232, thereby preventing the escape of actuation fluid from actuation chamber 216. When the flow of actuation fluid into bladder 430 slows or stops, the pressure differential across cap 434 is reduced, and the bladder's bias causes it to retract to its open position, thereby opening outlet 232 and permitting actuation fluid to be dumped therefrom into compliance sac 12.

It is contemplated that a number of small orifices 432 can be employed, as long as they are sized to restrict fluid flow so that a sufficient pressure differential can develop quickly across cap 434 to expand bladder 430.

In order to optimize the efficiency of pump 220, a mechanism is provided whereby a substantially constant maximum pressure differential across cap 434 is maintained. This comprises a number of pressure-actuated valves 436 in cap 434. Each valve 436 may take the form of an aperture 438 covered by a leaf spring shutter 440 attached to cap 434 along one edge thereof. When the fluid pressure within bladder 430 exceeds a certain predetermined value, the spring bias of shutters 440 will be overcome and fluid will begin to flow into actuation chamber 216 through valves 436. The amount of fluid flowing through valves 436 is a function of the deflection of shutters 440. Shutters 440 will open to the extent necessary to maintain a substantially constant maximum pressure differential across cap 434. If desired, orifice 432 may be provided with a shutter which partially covers its opening.

FIGS. 9 through 13 illustrate another embodiment of a flow responsive dump valve. The valve will be described in connection with the left ventricle. The figures illustrate the half of housing 210 which defines the actuating chamber 216. A manifold 240 is formed on housing 210. Actuator fluid is admitted into manifold 240 through an inlet nipple 242 which is adapted to be connected to flexible duct 224.

Figure 9:
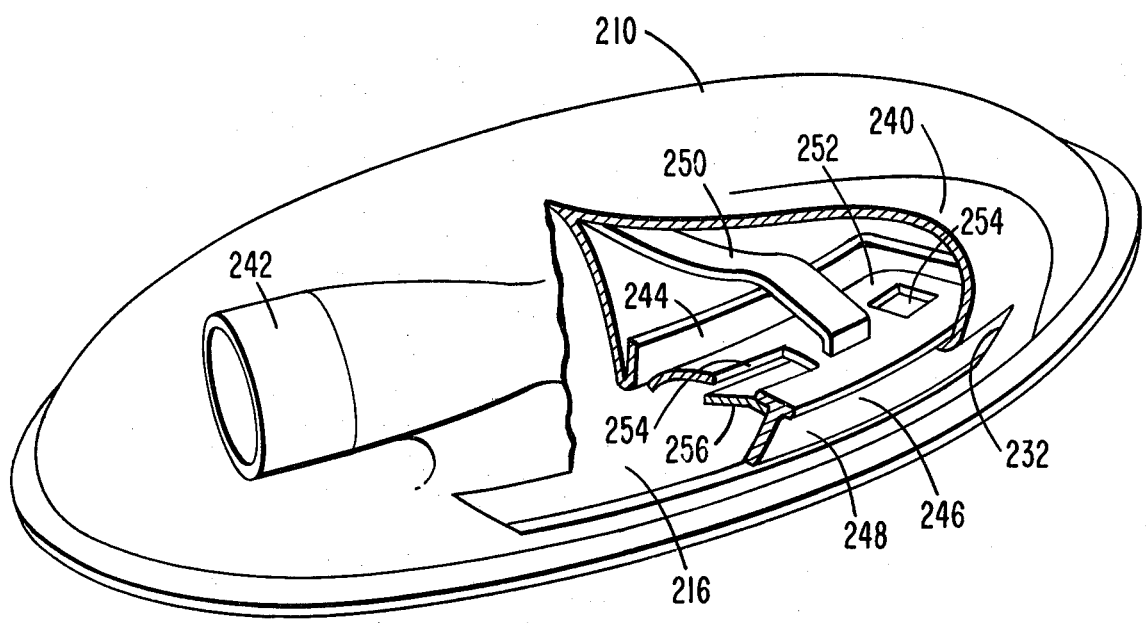
FIG. 9 is a perspective view, partly in section, of a TCP actuator housing having integral therein another embodiment of a flow responsive ventricular dump valve.
Figure 10:
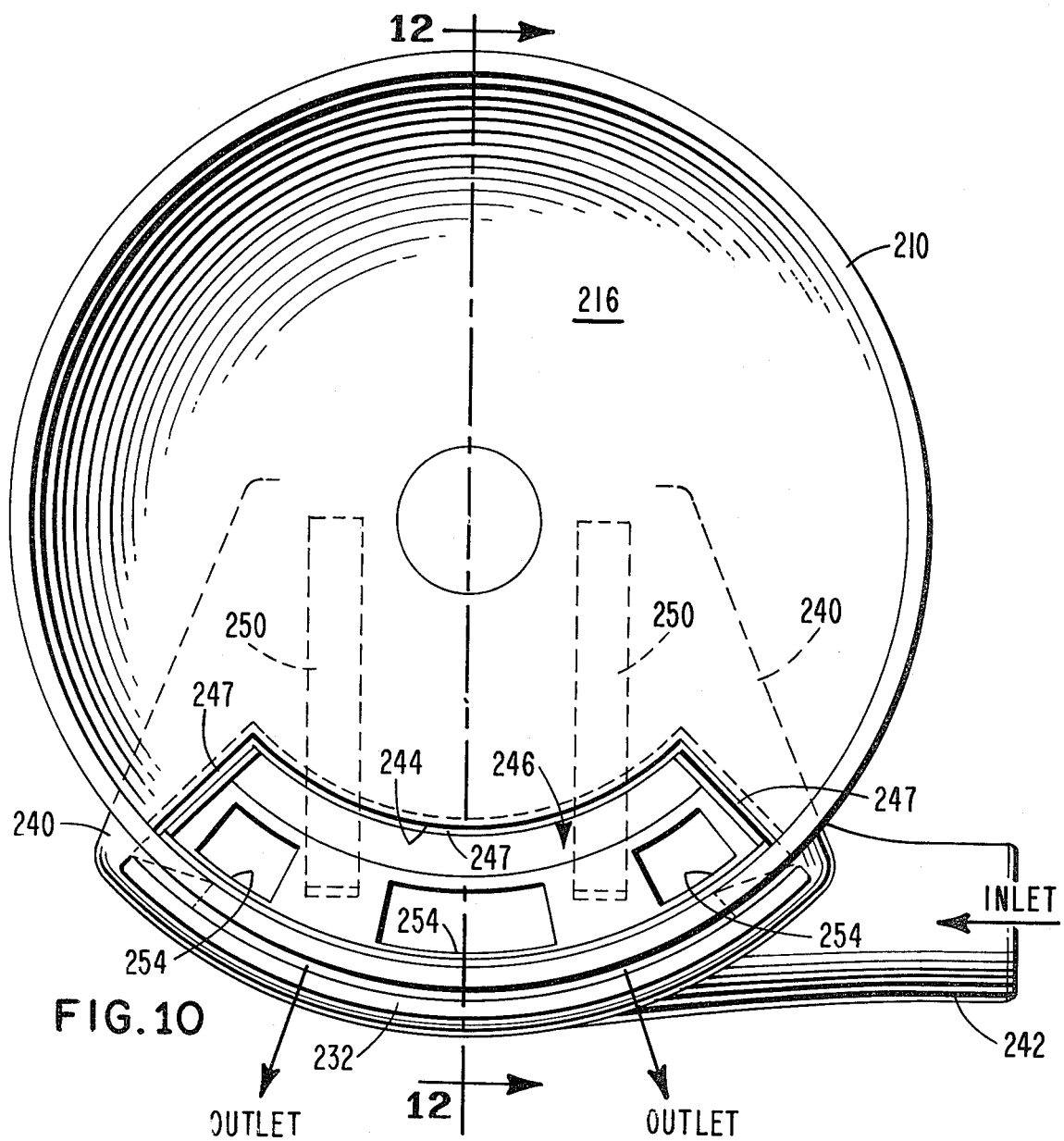
FIG. 10 is a bottom plan view of the structure shown in FIG. 9.
Figure 11:
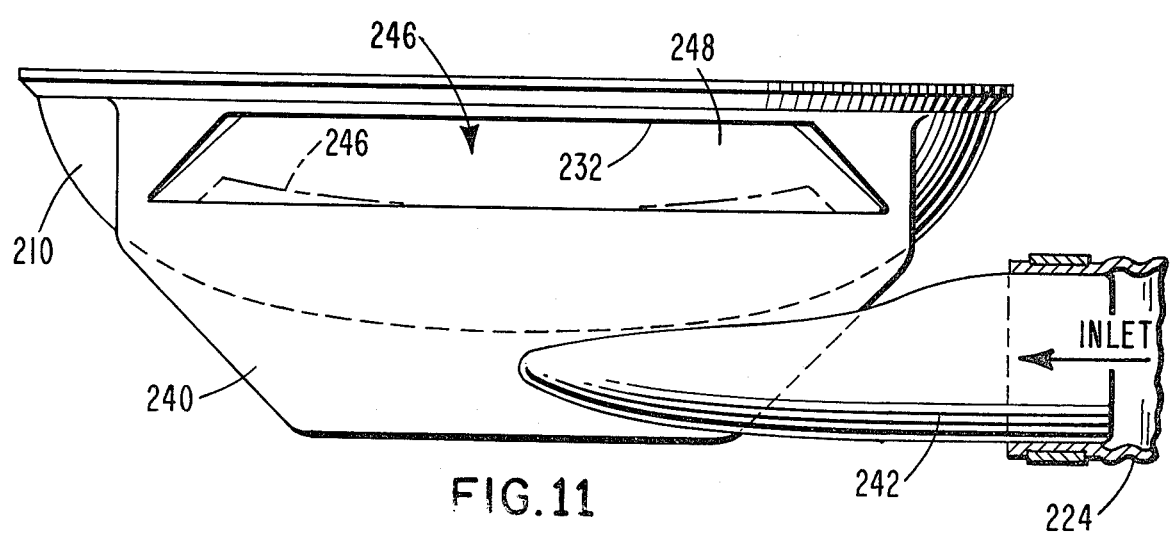
FIG. 11 is a side elevational view of the structure shown in FIG. 9.

The interior of manifold 240 and the interior of actuating chamber 216 communicate by way of an elongated arcuate channel 244. An L-shaped arcuate valve piston 246 substantially fills the space within channel 244. A narrow slit 247 on the inner radius and sides of valve piston 246 remains for the fluid to flow from manifold 340 into actuating chamber 216. One leg 248 of piston 246 is adapted to cover and close arcuate outlet 232 formed in manifold 240 when the valve piston 246 moves downwardly as illustrated in FIG. 9. Valve piston 246 is supported for arcuate movement within channel 244 on a pair of leaf springs 250 which are secured at one end to the interior of manifold 240 and at the other end to the top portion 252 of valve piston 246. Leaf springs 250 bias valve piston 246 in an upward direction, i.e., in a direction which will normally leave outlet 232 open. Valve piston 246 and leaf springs 250 are formed of a suitable metallic or plastic material, such as stainless steel or glass or carbon fiber reinforced plastic.

In operation, when actuator pump 220 delivers actuating fluid to manifold 240, the fluid flows into actuating chamber 216 through the narrow slit surrounding valve piston 246. When a sufficient pressure differential across valve piston 246 has developed to overcome the bias of leaf springs 250, valve piston 246 is forced downwardly to close outlet 232. When the flow of actuation fluid into manifold 240 slows or stops, the pressure differential across valve piston 246 is reduced, and the force of springs 250 causes valve piston 246 to move back to its open position, thereby opening outlet 232 and permitting actuation fluid to be dumped therefrom into compliance sac 12.

In order to optimize the efficiency of pump 220, a mechanism is provided whereby a constant pressure differential across valve piston 246 is maintained. This comprises a set of three apertures 254 in the top surface of valve piston 246. Apertures 254 are closed by leaf spring shutters 256 which flex downwardly to open apertures 254 for added fluid flow into actuating chamber 216 when the pressure of actuator fluid within manifold 240 exceeds a certain predetermined value. The greater the pressure within manifold 240, the greater the deflection of shutters 256, thereby maintaining the maximum pressure differential across valve piston 246 substantially constant.

The above-described valve can be designed to close at pressure drops across the piston which correspond to minimum flow rates of from about 3 to 7 liters per minute. Typically, times for complete closure of this valve should be in the range of from about 10 to 50 milliseconds. The valve opening time is governed by how quickly the volume of fluid swept by the piston can pass back through the slit into the actuation chamber. In valve closing the fluid can fill the actuation chamber of the ventricle while in valve opening it is assumed that fluid cannot flow back into the pump. Typical valve opening times (to full open position) on the order of from about 20 to 80 milliseconds are suitable for a valve of this design.

While the above description refers to a single dump valve associated with a single actuation chamber, it will, of course, be recognized that two or more dump valves of the same or different configurations can be associated with a single actuation chamber. While the above description refers generally to independently operable dump valves associated with each actuation chamber of a TCP, it is, of course, possible to utilize dump valves which operate in a mutually dependent manner by providing suitable coupling means.

CONTROL AND OPERATION

The above-described TCP system, especially in the preferred embodiments thereof, is particularly advantageous in its ability to respond to electronic controls which are designed to cause operation of the TCP in a manner consistent with natural heart operation in humans. Basically, a modified Frank-Starling mechanism is the sole means of blood pump response to the physiological needs of the implant recipient. Each blood pump ejects whatever blood fills it, and as a result, the atrial pressure is related to cardiac output in the manner similar to the Frank-Starling response of the normal heart. Under the Frank-Starling mechanism, cardiac output is equal to venous return. Since cardiac output is equal to the heart rate times stroke volume, changes in cardiac output can be achieved either by changing the heart rate or the stroke volume. It is preferred according to the present invention to keep the stroke volume constant and achieve changes in cardiac output by changing heart rate. Constant stroke volume may be achieved by intrinsic means, e.g., by use of a stroke-limiting diaphragm, or by providing extrinsic control of diaphragm excursions in a known manner.

In the preferred embodiment of FIG. 3, heart rate control is effected by delivering controlled intermittent pulses of actuation fluid to the actuation chamber in response to a control signal supplied to each actuation fluid pump motor by control circuit C (FIG. 1). This control signal starts and stops (or speeds up and slows down) the pumps to cause the ventricular dump valves to close and open in the manner described above at the beginning and end of systole. This control signal can be generated in response to any of a number of known measurable variables which provide information that can be employed to effect blood pump operation to ensure that the physiologic requirements of blood flow are met. One such variable is atrial pressure, which can be measured in a known manner using pressure transducers. Landis et al., "Long-Term In Vivo Automatic Electronic Control of the Artificial Heart", *Trans. ASAIO*, Vol. XXIII, pp. 519-525, 1977, herein incorporated by reference.

In the embodiment of FIG. 5, alternately pulsatile operation can be controlled by supplying a control signal to the motor operated switching valve which governs the destination and duration of each fluid pulse.

In the preferred manner of operating the TCP of the present invention, ventricular ejections will alternate thereby conserving actuation fluid. As indicated previously, however, copulsatile operation can be effected with a concomitant increase in the hydraulic reservoir capacity. One of the significant advantages of the preferred TCP design of the present invention is that by the use of separate actuation mechanisms for each ventricle, separate and optimal control of each ventricle can be achieved.

POWER SUPPLY

In the preferred embodiment power to energize the electric motors and control electronics is furnished by electromagnetic induction across the intact skin of the patient. Telemetry signals for indicating system and patient information are also transmitted in this manner, albeit usually in the opposite direction. This type of power supply and telemetering system has been described in the prior art and consists generally of a high frequency coupling transformer which includes a small flat internal coil implanted subcutaneously and a larger flat external coil which is mounted over the implanted coil. The external coil can be carried in a vest, belt or other article of clothing. In practice, this energy transmission system can tolerate considerable movement of the external coil relative to the internal coil without adversely affecting the transfer of power or information into or out of the system. Power to drive the external coil can be provided in an external electronics pack which can contain batteries, battery charging electronics and other electronic systems useful in the monitoring of system and patient functions. Also included in the monitoring electronics are provisions for audible or visible alarms which warn of incipient malfunction or problems.

The external battery pack can be designed to provide several hours of mobility for the patient. This battery pack when depleted can be easily replaced with a fully charged one. It can also be charged from AC line current when the patient is "plugged into the wall" or while the patient is using another battery pack, or from an automative DC battery while motoring.

An implanted internal battery pack will also provide a temporary source with complete freedom from any external power. This will permit the recipient to undertake acts such as bathing and the like and will provide sufficient time to change external power sources, i.e., changing the vest or external battery packs. In the preferred embodiment this internal battery will be located subcutaneously for easier periodic replacement.

While certain specific embodiments of the invention have been described with particularity herein, it should be recognized that various modifications thereof will appear to those skilled in the art. Therefore, the scope of the invention is to be limited solely by the scope of the claims appended hereto.

We claim:

1. An implantable hydraulic actuation system for supplying motive power to a blood pumping chamber having a flexible portion comprising:
    an actuation fluid reservoir;
    actuation fluid pumping means in fluid communication with said reservoir for providing intermittent pulses of actuation fluid;
    an actuation chamber having an actuation fluid inlet path in fluid communication with said pumping means, and a separate actuation fluid outlet path in fluid communication with said reservoir; said actuation chamber being adapted to cause displacement of the flexible portion of said blood pumping chamber in response to changes in volume of actuation fluid in said actuation chamber; and
    valve means associated with said actuation chamber adapted to close or open said actuation fluid outlet path primarily in response to forces which vary as a function of actuation fluid flow through said actuation fluid inlet path.

2. An implantable hydraulically actuated blood pumping system comprising:

a blood pumping chamber having a blood inlet, a blood outlet and a flexible portion;

an actuation fluid reservoir;

actuation fluid pumping means in fluid communication with said reservoir for providing intermittent pulses of actuation fluid;

an actuation chamber having an actuation fluid inlet path in fluid communication with said pumping means, and a separate actuation fluid outlet path in fluid communication with said reservoir, said actuation chamber being operatively associated with said blood pumping chamber to cause displacement of said flexible portion of said blood pumping chamber in response to changes in volume of actuation fluid in said actuation chamber; and valve means associated with said actuation chamber adapted to close or open said actuation fluid outlet path primarily in response to forces which vary as a function of actuation fluid flow through said actuation fluid inlet path whereby said actuation chamber fills with actuation fluid and blood is expelled from said associated blood pumping chamber while said valve means is closed, and actuation fluid drains from said actuation chamber and said associated blood pumping chamber is allowed to fill with blood while said valve means is open.

3. An implantable hydraulically actuated total cardiac prosthesis comprising:

a pair of blood pumping chambers each having a blood inlet, a blood outlet and a flexible portion;

a pair of actuation chambers each having an actuation fluid inlet path and a separate actuation fluid outlet path, one of said actuation chambers being operatively associated with one of said blood pumping chambers and the other of said actuation chambers being operatively associated with the other of said blood pumping chambers to cause displacement of the flexible portion of said blood pumping chambers in response to changes in volume of actuation fluid in their associated actuation chambers;

an actuation fluid reservoir in fluid communication with said actuation fluid outlet paths;

actuation fluid pumping means in fluid communication with said reservoir and said actuation fluid inlet paths for providing intermittent pulses of actuation fluid from said reservoir to said actuation chambers;

and valve means associated with said actuation chambers adapted to close or open said actuation fluid outlet path primarily in response to forces which vary as a function of actuation fluid flow through said associated actuation fluid inlet path whereby said actuation chamber fills with actuation fluid and blood is expelled from said associated blood pumping chamber while said valve means is closed, and actuation fluid drains from said actuation chamber and said associated blood pumping chamber is allowed to fill with blood while said valve means is open.

4. The invention of claims 1, 2 or 3 wherein said actuation fluid reservoir comprises a compliant zone defined at least in part by a flexible wall portion made from biocompatible elastomeric material.

5. The invention of claim 4 wherein said actuation fluid reservoir also includes flexible ducting leading to and from said actuation fluid pumping means and to and from said actuation chamber.

6. The invention of claim 3 wherein said actuation fluid reservoir comprises a separate compliant zone associated with each of said actuation chambers, defined at least in part by a flexible wall portion made from biocompatible elastomeric material, said compliant zones communicating with each other, said pumping means and said actuation chambers by flexible ducting.

7. The invention of claims 1 or 2 wherein said actuation fluid pumping means comprises a pump and drive motor therefor.

8. The invention of claim 7 wherein said pump is a high speed, mixed flow rotary pump.

9. The invention of claim 7 wherein said drive motor is a brushless DC electric motor.

10. The invention of claim 9 further comprising means for commutating said brushless DC electric motor.

11. The invention of claim 10 wherein said means for commutating comprises back-emf control circuitry.

12. The invention of claim 3 wherein said actuation fluid pumping means comprises a separate pump and drive motor therefor associated with each of said actuation chambers.

13. The invention of claim 12 wherein each of said pumps is a high speed, mixed flow rotary pump.

14. The invention of claim 12 wherein each of said drive motors is a brushless DC electric motor.

15. The invention of claim 14 further comprising means for commutating said brushless DC electric motor.

16. The invention of claim 15 wherein said means for commutating comprises back-emf control circuitry.

17. The invention of claim 3 wherein said actuation fluid pumping means comprises a pump and drive motor therefor and a three-way switching valve associated with the pump outlet for alternately directing the pump output to one or the other of said actuation chambers.

18. The invention of claim 17 wherein said pump is a high speed, mixed flow rotary pump.

19. The invention of claim 17 wherein said drive motor is a brushless DC electric motor.

20. The invention of claim 19 further comprising means for commutating said brushless DC electric motor.

21. The invention of claim 20 wherein said means for commutating comprises back-emf control circuitry.

22. The invention of claim 17 wherein said three-way switching valve has a separate drive motor associated therewith.

23. The invention of claims 2 or 3 wherein said blood inlet and said blood outlet are provided with prosthetic valves adapted to permit the flow of blood in only one direction.

24. The invention of claims 2 or 3 wherein said blood pumping chamber comprises a variable volume zone defined in part by a flexible membrane made from biocompatible elastomeric material and in part by a rigid blood pumping chamber housing.

25. The invention of claims 1, 2 or 3 wherein said actuation chamber comprises a variable volume zone defined in part by said flexible portion of said blood pumping chamber and in part by a rigid actuation chamber housing.

26. The invention of claims 1, 2 or 3 wherein said valve means is adapted:
   to close said actuation fluid outlet path at the beginning of each of said fluid pulses when sufficient flow of actuation fluid is supplied to said actuation fluid inlet path to create forces above a predetermined threshold magnitude;
   to keep said actuation fluid outlet path closed during said pulses while said flow through said inlet path is sufficient to maintain said forces above said predetermined threshold magnitude; and
   to open said actuation fluid outlet path at the end of said pulses when said flow through said inlet path is reduced to a value at which said forces fall below said predetermined threshold magnitude.

27. The invention of claim 26 wherein said valve means includes means for exerting a permanent bias force tending to open said actuation fluid outlet path, and the magnitude of said bias force is equal to said predetermined threshold.

28. The invention of claim 27 wherein said valve means is adapted to act in response to pressure forces created by the flow of actuation fluid through said inlet path.

29. The invention of claim 28 wherein said valve means comprises a hollow closure member having an interior in fluid communication with actuation fluid delivered by said pumping means, and movable between a closed position blocking said actuation fluid outlet path when filled with actuation fluid during fluid pulses, and an open position clear of said actuation fluid outlet path between fluid pulses.

30. The invention of claim 29 wherein said closure member comprises an expandable envelope.

31. The invention of claim 30 wherein said envelope comprises elastomeric material.

32. The invention of claim 27 wherein said valve means comprises a closure member in said fluid inlet path and movable between a closed position blocking said fluid outlet path during fluid pulses, and an open position clear of said actuation fluid outlet between fluid pulses.

33. The invention of claim 32 wherein said valve means is adapted to act in response to differential pressure forces.

34. The invention of claim 33 wherein said fluid inlet path includes at least one orifice through said closure member through which actuation fluid flows from said pumping means into said actuation chamber.

35. The invention of claim 34 wherein said closure member is hollow and has an interior in fluid communication with actuation fluid delivered by said pumping means, and said orifice is formed through the wall of said hollow closure member.

36. The invention of claim 35 wherein said closure member comprises an expandable envelope.

37. The invention of claim 36 wherein said orifice is formed through a substantially rigid wall portion of said envelope.

38. The invention of claim 37 wherein said envelope comprises elastomeric material.

39. The invention of claim 36 wherein said envelope comprises elastomeric material.

40. The invention of claim 34 further comprising means for maintaining a substantially constant pressure differential across said closure member during fluid pulses despite changes in flow rate of fluid along said fluid inlet path.

41. The invention of claim 40 wherein said means for maintaining a substantially constant pressure differential comprises at least one aperture through said closure member, and shutter means biased to substantially close said aperture, but movable to open said aperture to an extent proportional to the flow rate of fluid along said fluid inlet path.

42. The invention of claim 41 wherein said shutter means comprises a leaf spring shutter overlying said aperture.

43. The invention of claim 41 wherein said closure member is hollow and has an interior in fluid communication with actuation fluid delivered by said pumping means, and said orifice and said aperture are formed through the wall of said hollow closure member.

44. The invention of claim 43 wherein said closure member comprises an expandable envelope.

45. The invention of claim 44 wherein said orifice and said aperture are formed through a substantially rigid wall portion of said envelope.

46. The invention of claim 45 wherein said envelope comprises elastomeric material.

47. The invention of claim 44 wherein said envelope comprises elastomeric material.

48. The invention of claim 2 or 3 further comprising means for applying electric power to said actuation fluid pumping means and associated control electronics in a patient having an implanted cardiac prosthesis.

49. The invention of claim 48 wherein said means for supplying electric power comprises an external primary coil inductively coupled to a subcutaneous secondary coil for transmitting electrical energy across the intact skin of said patient.

50. A method of actuating an implantable blood pump comprising a blood pumping chamber having a blood inlet, a blood outlet, and a flexible portion, and an actuation chamber operatively associated with said blood pumping chamber having an actuation fluid inlet path, an actuation fluid outlet path and valve means associated with said actuation fluid outlet path, comprising the steps of:
   (a) delivering intermittent pulses of actuation fluid to said actuation chamber through said actuation fluid inlet path; and
   (b) alternately closing and opening said actuation fluid outlet path with said valve means in response to forces which vary as a function of actuation fluid flow through said actuation fluid inlet path to cause said actuation chamber to fill with actuation fluid and blood to be expelled from said blood pumping chamber while said valve means is closed, and to cause said actuation fluid to drain from said actuation chamber and blood to fill said blood pumping chamber while said valve means is open.

51. A method of actuating an implantable blood pump comprising a blood pumping chamber having a blood inlet, a blood outlet, and a flexible portion, and an actuation chamber operatively associated with said blood pumping chamber having an actuation fluid inlet path, an actuation fluid outlet path and valve means associated with said actuation fluid outlet, comprising the steps of:
   (a) delivering intermittent pulses of actuation fluid to said actuation chamber through said actuation fluid inlet path;
   (b) closing said actuation fluid outlet path with said valve means at the beginning of each fluid pulse, by supplying sufficient flow of actuation fluid through said inlet path to create forces on said valve means above a predetermined threshold magnitude;

(c) maintaining said actuation fluid outlet path closed with said valve means during each fluid pulse by continuing to supply sufficient flow of actuation fluid through said inlet path to maintain said forces at or above said predetermined threshold magnitude to cause actuation chamber to fill with actuation fluid and blood to be expelled from said blood pumping chamber during said fluid pulse; and (d) opening said actuation fluid outlet path with said valve means at the end of each fluid pulse by reducing the flow of actuation fluid through said inlet path to cause said forces to fall below said predetermined threshold magnitude, to cause said actuation fluid to drain from said actuation chamber and blood to fill said blood pumping chamber between said fluid pulses.

52. A method of actuating an implantable total cardiac prosthesis having a pair of compressible blood pumping chambers each having a blood inlet, a blood outlet and a flexible portion, a separate actuation chamber operatively associated with each blood pumping chamber, each actuation chamber having an actuation fluid inlet path, an actuation fluid outlet path, and valve means associated with each actuation fluid outlet path, comprising the steps of:

(a) delivering intermittent pulses of actuation fluid to said actuation chambers through said actuation fluid inlet paths;

(b) alternately closing and opening the actuation fluid outlet path of said actuation chambers with said valve means in response to forces which vary as a function of actuation fluid flow through said actuation fluid inlet paths to cause said actuation chambers to fill with actuation fluid and blood to be expelled from said blood pumping chambers while said valve means is closed, and to cause said actuation fluid to drain from said actuation chambers and blood to fill said blood pumping chambers while said valve means is open.

53. The method of claim 52 wherein said total cardiac prosthesis is operated in an alternately pulsatile fashion by alternate intermittent pulses of actuation fluid to first one and then the other of said actuation chambers.

54. The method of claim 52 wherein said total cardiac prosthesis is operated in copulsatile fashion by supplying intermittent pulses of actuation fluid to both of said actuation chambers at substantially the same time.

55. The method of claims 50, 51 or 52 wherein the steps of opening and closing of said valve means comprise utilizing the pressure forces created by the flow of actuation fluid through said actuation fluid inlet path.

56. The method of claim 55 wherein said pressure forces are differential pressure forces.

* * * * *